United States Patent [19]

Gelbwachs

[11] Patent Number: 4,516,858

[45] Date of Patent: May 14, 1985

[54] MULTIPLE SITE LASER EXCITED POLLUTION MONITORING SYSTEM

[75] Inventor: Jerry A. Gelbwachs, Manhattan Beach, Calif.

[73] Assignee: The United States of America as represented by the Secretary of the Air Force, Washington, D.C.

[21] Appl. No.: 347,391

[22] Filed: Feb. 9, 1982

[51] Int. Cl.³ ............................................. G01N 21/01
[52] U.S. Cl. ..................................... 356/437; 250/227
[58] Field of Search ............... 356/432, 437, 438, 439; 250/227; 340/632, 630, 815.31

[56] References Cited

U.S. PATENT DOCUMENTS

| | | | |
|---|---|---|---|
| 3,697,185 | 10/1972 | Kassel et al. | 356/410 |
| 3,781,092 | 12/1973 | Sussman et al. | 250/227 X |
| 3,820,897 | 6/1974 | Roess | 356/75 |
| 3,820,901 | 6/1974 | Kreuzer | 356/97 |
| 3,948,345 | 3/1976 | Rosencwaig | 181/5 |
| 4,028,932 | 6/1977 | Rosencwaig | 73/67.2 |
| 4,044,257 | 8/1977 | Kreuzer | 250/343 X |
| 4,067,653 | 1/1978 | Fletcher | 356/204 |
| 4,120,592 | 10/1978 | Fleming et al. | 356/201 |
| 4,236,827 | 12/1980 | Horiba et al. | 356/437 |
| 4,409,476 | 10/1983 | Lofgren et al. | 250/227 |
| 4,459,024 | 7/1984 | Gergely | 356/338 |

FOREIGN PATENT DOCUMENTS

| | | | |
|---|---|---|---|
| 146098 | 1/1981 | German Democratic Rep. | 356/437 |
| 54-5778 | 1/1979 | Japan | 356/437 |

OTHER PUBLICATIONS

Loper, G. L. et al, "Carbon Dioxide Laser Absorption Spectra and Low ppb Photoacoustic Detection of Hydrazine Fuels", *Applied Optics*, vol. 19, No. 16, 15 Aug. 1980, pp. 2726-2734.

Suarez, Leo, "A Multicomponent Infrared Ambient Air Monitor", *ISA Transactions*, vol. 18, No. 1, 1979, pp. 3-8.

Kreuzer, L. B. et al, "Air Pollution: Sensitive Detection of Ten Pollutant Gases by Carbon Monoxide and Carbon Dioxide Lasers", *Science*, vol. 177, 28 Jul. 1972, pp. 347-349.

*Primary Examiner*—Vincent P. McGraw
*Attorney, Agent, or Firm*—Donald J. Singer; Jacob N. Erlich

[57] ABSTRACT

A multiple site laser excited pollution monitoring system having a single laser located at a central location capable of providing a laser output beam, deflected in timed sequence, in a plurality of distinct different directions. Transmitting means, preferably in the form of a plurality of optical fibers, transmit the laser output beam in timed sequence to a plurality of remotely located laser excited pollution detectors (photoacoustic detector heads). Signals from the pollution detectors are transmitted to a signal processor and display unit also located at the central location. As a consequence thereof, a single laser can provide power for a plurality of laser excited detectors at a multiplicity of remote sites and thereby greatly reduce the expense involved in detecting the presence of pollutants at each of the plurality remote locations.

6 Claims, 3 Drawing Figures

MULTIPLE SITE LASER EXCITED POLLUTION MONITORING SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates generally to pollution monitoring systems, and, more particularly to a laser excited pollution monitoring system capable of performing vapor analysis at a plurality of remote locations.

A critical need exists for toxic vapor detection at various locations in, for example, a rocket launch installation. During routine handling operations, at such rocket launch installations, the possibility exists that volatile compounds such as hydrazine, monomethylhydrazine (MMH), and unsymmetrical dimethylhydrazine (UDMH) which are extensively used as rocket fuels can be inadvertently released into the ambient air. The health hazard to humans resulting from exposure to airborne hydrazines, even at very low concentrations, are of increasingly great concern. New standards have been proposed that will reduce the maximum allowable concentrations of hydrazine, MMH, and UDMH in work place ambient air samples, collected over a two hour period, to 30, 40, and 60 PPB, respectively.

The photoacoustic toxic vapor detector is an example of a toxic vapor detector which has been successful in detecting minute quantities of toxic vapors from volatile compounds used as rocket fuel. The detection principle utilized in the photoacoustic vapor detector is based upon the use of an audio-frequency modulated laser, tuned to an absorption frequency of the molecules under test. The laser produces a beam of electromagnetic radiation which irradiates a vessel or cell in which the molecules of the toxic vapor are located. The molecules of the toxic vapor absorb the laser light and reach an excited state. Collisions with the ambient air molecules deactivate the excited molecules thereby causing a periodic pressure rise inside the cell. This periodic pressure rise is in the form of a sound wave capable of being detected by a pressure transducer located within the cell. A more detailed description of such a photoacoustic detector can be found in an article by L. B. Kreuzer et al entitled "Air Pollution: Sensitive Detection of Ten Pollutant Gases by Carbon Monoxide and Carbon Dioxide Lasers," *Science,* Volume 177, July 28, 1972, pages 347–349.

Unfortunately, the utilization of the photoacoustic detection technique at, for example, rocket launch installation sites, is impractical because of the need of multiple monitoring points throughout the site. This impracticality arises as a result of the requirement of positioning the laser source, photoacoustic head including the cell and signal processor at each monitoring point.

The major portion of the expense of providing a complete photoacoustic detector is the laser. For example, a typical laser capable of being utilized within a photoacoustic detector would be a tunable $CO_2$ laser. Its cost, however, represents approximately 80% of the total cost of the photoacoustic detector. In addition, the laser is also a major contributor to the size and weight of the unit. Hence, the placement of a complete photoacoustic detector unit at each site results in a monitoring network that is bulky, extremely expensive, difficult to maintain, and as pointed out hereinabove, totally impractical.

It is therefore essential in order to effectively protect personnel at rocket launch sites and the like to provide a toxic vapor detection system which is not only capable of incorporating therein the photoacoustic detection technique, but is also capable of utilizing this technique in an effective and economical manner at a multitude of monitoring sites. In addition, the system should have rapid response, be rugged and highly reliable in operation.

SUMMARY OF THE INVENTION

The present invention overcomes the problems encountered in the past and as set forth in detail hereinabove by providing a multiple site laser excited pollution monitoring system which includes the benefits of the photoacoustic detection technique. In addition, the present invention is also applicable with any vapor detection technique that requires laser excitation. Such detection methods may include those based upon Raman scattering, fluorescence, absorption and photoionization.

The remote pollution monitoring system of this invention incorporates therein a single laser or single laser bank located at a central location. The single laser or single laser bank delivers output power at predetermined wavelengths to a plurality of detector heads located remotely from the central location. Since only one suitable laser is required to provide the molecular excitation for the photoacoustic detector head, a cost reduction of approximately 80% as well as substantial reduction of size and weight can be maintained. This invention, therefore, completely eliminates the need for a tunable laser at each detection site.

With the present invention, the laser is located along with the monitoring panels and signal processor at a single central location. Optical fibers are utilized to carry the laser power to each of a plurality of, for example, photoacoustic detector heads at the remote monitoring sites. Since the optical fibers are small and rugged they can be installed along side the wires that transmit the electrical signals from the photoacoustic head back to the signal processor at the central location.

A beam deflector is positioned between the laser and the optical fiber input. The deflector serves to sequentially direct the laser beam with CW power into each optical fiber for a portion of the audio period. The waveform is transmitted through the optical fiber to the detector head at the remote monitoring site. Measurement of the vapor concentration is performed by synchronous detection of the fundamental of the acoustic wave in the photoacoustic cell of the detector head in the manner indicated above.

The portion of the laser excitation that is effective in exciting the molecules is given by the fundamental component of the input waveform. Each of the plurality n of photoacoustic heads receives the identical fundamental power waveform, each slightly displaced in time. The peak amplitude of the fundamental power at each remote site is $(2/\pi) \sin(\pi/n)$ of the CW power coming out of the deflector less the transmission losses of the optical fibers. Thus, by utilizing time-multiplexing and optical fibers, a single laser can service many detector heads at remote locations.

The ratio of the fundamental frequency component signal to the power is then transmitted by electrical wire to a signal processor located at the central location. The signal processor converts the electrical impulses into appropriate gaseous concentrations which are then displayed at the central location.

It is therefore an object of this invention to provide a laser excited pollution monitoring system capable of operating at multiple remote locations.

It is another object of this invention to provide a laser excited photoacoustic multiple site pollution monitoring system which is capable of monitoring toxic rocket fuels and their toxic air oxidation products at the threshold limiting value of 0.01–0.1 ppm range.

It is a further object of this invention to provide a multiple site pollution monitoring system which possesses the flexibility to detect new toxic vapors once they are identified.

It is still a further object of this invention to provide a laser excited multiple site pollution monitoring system which is economical to produce and which utilizes conventional, currently available components that lend themselves to standard mass producing manufacturing techniques.

For a better understanding of the present invention, together with other and further objects thereof, reference is made to the following description taken in conjunction with the accompanying drawing and its scope will be pointed out in the appended claims.

DETAILED DESCRIPTION OF THE DRAWING

DETAILED DESCRIPTION OF THE PREFERRED EMBODIMENT

Figure 1:
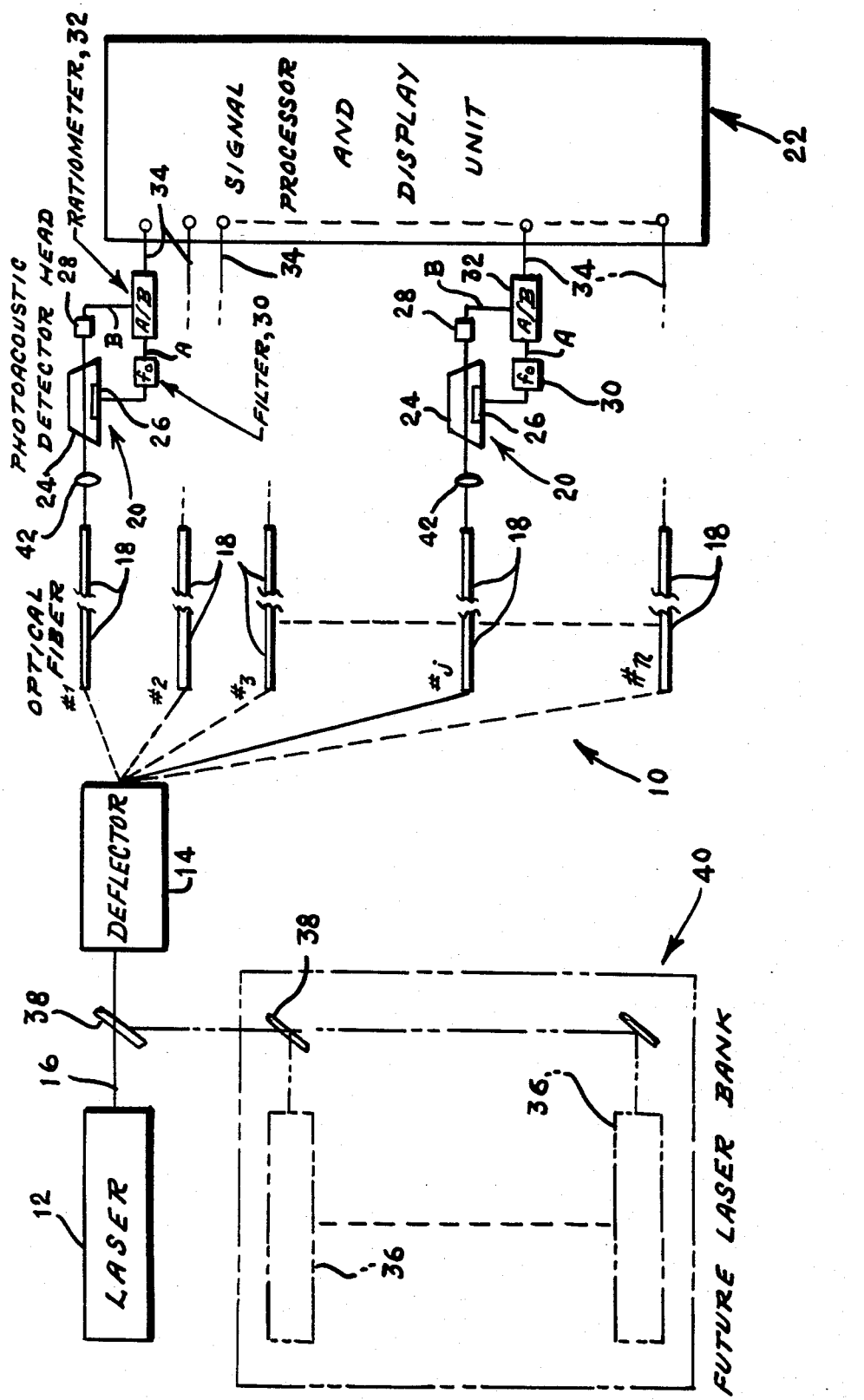
FIG. 1 is a schematic representation of the multiple site laser excited pollution monitoring system of this invention.

Reference is now made to FIG. 1 of the drawing which schematically illustrates the multiple site laser excited pollution monitoring system 10 of this invention. System 10 of this invention provides multi-site photoacoustic detection of pollutants, preferably toxic vapors, with only the detector head at the remote site. It should be realized, however, that although this invention is described in conjunction with the photoacoustic detection technique, such a system is also applicable to any pollution detection method that requires laser excitation. Such methods may be based upon Raman scattering, fluorescence, absorption, and photoionization.

There are five main components which make up the pollution monitoring system 10 of this invention. These include a suitable source of electromagnetic radiation in the form of, for example, a $CO_2$ laser 12; a time controlled deflector 14 which may, for example, be in the form of a rotating mirror, an acousto-optic deflector, or an electro-optic deflector; a plurality of transmitting elements, such as optical fibers 18; a plurality of detector heads, such as, for example photoacoustic detector heads 20; and a conventional signal processor and display unit 22.

Deflector 14 redirects in a timed sequence the output 16 of laser 12 into each of the plurality of optical fibers 18. Fibers 18 sequentially transmit the output 16 of laser 12 to a plurality of remote locations, respectively, at which are situated the photoacoustic detector heads 20. The signal processor and display unit 22 although shown in FIG. 1 of the drawing as being adjacent detector heads 20, in actuality is situated at a central location at which laser 12 is also located. Signal processor and display unit 22 receives signals from the plurality of photoacoustic detector heads 20 and outputs a display of the pollutant quantities at the plurality of remote sites.

Specific reference is now made to photoacoustic detector head 20, a plurality of which are located at a plurality of remote sites, respectively, at which the pollutants in the form of, for example, toxic vapors are to be analyzed. The photoacoustic detector head 20 is a conventional device more fully described by L. B. Kreuzer et al in the already referred to article entitled "Air Pollution: Sensitive Detection of Ten Pollutant Gases by Carbon Monoxide and Carbon Dioxide Lasers," *Science*, Volume 177, July 28, 1972, pages 347–349.

The major components of photoacoustic detector head 20 include a photoacoustic cell 24 which is preferably in the form of a small enclosed vessel having an opening therein for accepting pollutants. Laser 12 is utilized to irradiate the interior of cell 24. Situated within photoacoustic cell 24 is a conventional pressure transducer 26 which is capable of detecting soundwaves generated by a periodic pressure rise within cell 24 caused by the collision between ambient air molecules and the laser excited molecules of the pollutants.

The power passing through cell 24 is monitored by a conventional detector in the form of, for example, a thermopile 28. The photoacoustic signal output from transducer 26 passes through any suitable narrow bandpass audio filter 30 centered at $f_o$ in order to extract therefrom the fundamental frequency component A. The output B from thermopile 28 as well as the output A are fed into a conventional ratiometer 32 which provides a ratio of the fundamental frequency component A to the power signal B, that is, the normalized photoacoustic response at $f_o$. This output A/B is transmitted by electrical wire 34 to a suitable signal processor and display unit 22 located at the central location.

Laser 12 utilized with this invention is situated at the central location at which is also located signal processor and display unit 22. This single tunable laser 12 provides an output 16 at a wavelength tuned to the absorption level of the molecules of the vapor to be detected by photoacoustic detector head 20. Deflector 14 systematically and in timed sequence directs output 16 to the plurality of optical fibers 18 for transmission to photoacoustic detector heads 20 situated at the remote locations.

In instances wherein various types of pollutants are to be detected it is possible to provide a plurality of different wavelengths. This can be accomplished either by using one tunable laser 12, multiple lasers 36, or a combination of the two in conjunction with appropriate directing means such as beam splitters 38 illustrated in phantom in FIG. 1 of the drawing as future laser bank 40. In this way laser outputs at a variety of wavelengths can be utilized with the photoacoustic detector heads 20.

MODE OF OPERATION

In operation the output 16 from laser 12 is directed in timed sequence by deflector 14 through optical fibers 18. The laser power exiting each optical fiber 18 at each remote site is focused by any conventional focusing means such as lens 42 into the photoacoustic cell 24 of photoacoustic detector head 20. The power passing through cell 24 is monitored by thermopile 28 and the output therefrom is referenced as B.

Within cell 24 the toxic vapor molecules under detection absorb the laser light and reach an excited state. Collision with the ambient air molecules deactivate the excited molecules thereby causing a periodic pressure rise inside cell 24. This periodic pressure rise is a sound wave that is detected by transducer 26 located within cell 24. The photoacoustic signal is then passed through narrow bandpass audio filter 30 centered at $f_o$ to extract the fundamental frequency component A. The ratio of this signal A to the power B, the normalized photoacoustic response at $f_o$, is then transmitted by electrical wires 34 to signal processor and display unit 22 at the central location. Signal processor and display unit 22 converts the electrical impulses into gaseous concentrations which are then displayed. A typical example of such a signal processor and display unit 22 that can be utilized with this invention can be found in an article by Leo Suarez entitled "A Multi-Component, Multi-Point Infrared Ambient Air Monitor," *ISA Transactions*, Volume 18, Number 1, 1979, pages 3 through 8.

Figure 2:
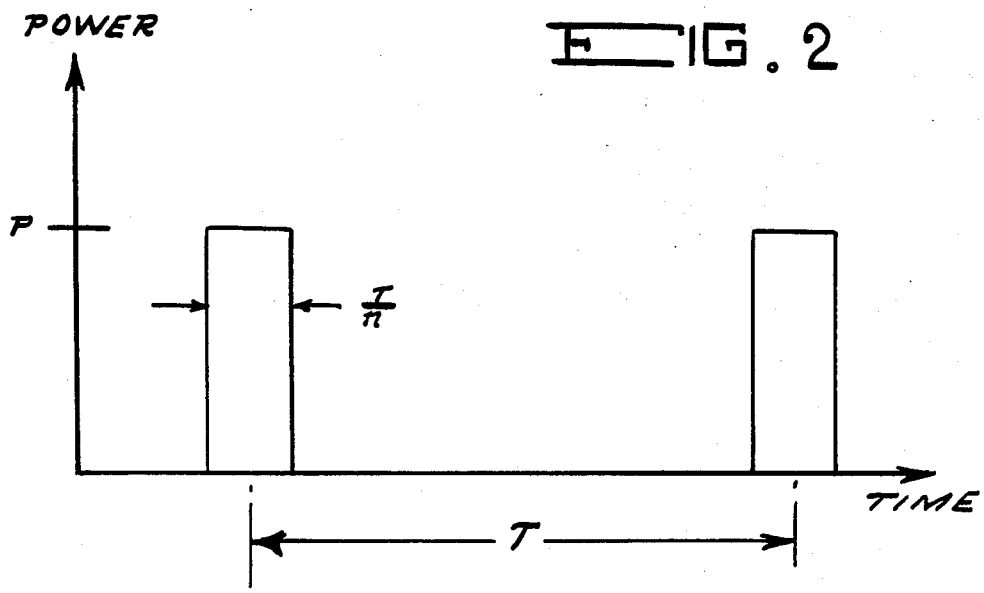
FIG. 2 is a graphic representation of the input power to a particular optical fiber of the multiple site laser excited pollution monitoring system of this invention.

FIG. 2 graphically represents the input power to the j optical fiber 18, for example. This wave form is transmitted through j optical fiber 18 to its corresponding detector head 20 at the remote monitoring site. Measurement of the vapor concentration is performed by synchronous detection at the beam deflecting frequency $f_o$. This frequency $f_o = 1/T$ where T = the time interval between successive laser input into the same fiber 18.

Figure 3:
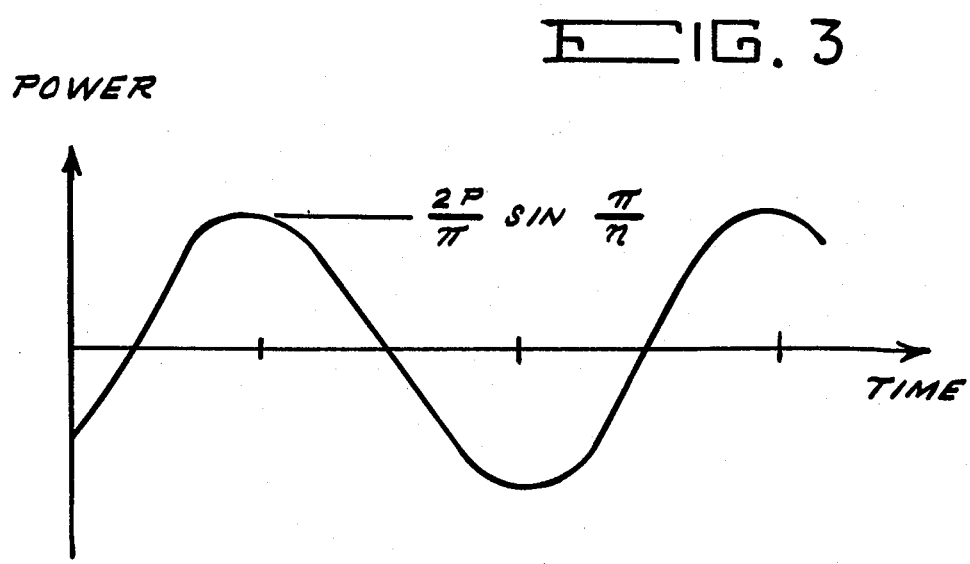
FIG. 3 is a graphic representation of the fundamental frequency component to a particular detector head of the multiple site laser excited pollution monitoring system of this invention.

The waveform shown in FIG. 2 can be decomposed into a d.c. term and sinusoidal components at $f_o$, the fundamental frequency, and the harmonics of $f_o$. The portion of the waveform shown in FIG. 2 that produces a response in the synchronous detector is the fundamental component. The fundamental frequency component at $f_o$ of the input waveform is obtained by performing a frequency decomposition (Fourier analysis). Results of such a decomposition are shown in FIG. 3 of the drawing.

It is therefore clearly evident that each of the n photoacoustic heads 20 receives the identical fundamental power wave form, each slightly displaced in phase. The peak amplitude of the fundamental power at each remote site is $(2/\pi) \sin(\pi/n)$ of the CW power coming out of deflector 14 less the transmission losses of optical fibers 18. Thereby, by time-multiplexing and the use of optical fibers 18, a single laser 12 can service many detector heads 20 at a variety of remote locations.

In addition if at a future date a requirement ever arises to increase the number of species to be monitored and that the new species require an excitation wavelength not available from laser 12, one can simply add additional lasers 36 at the central location as shown in FIG. 1. Thus the monitoring capability of this invention can be extended without disturbing the detector heads 20 in the field. Similarly, with advances in laser technology, new lasers can be easily substituted for the outdated models thus offering the potential for future improved performance at a reasonable cost.

Although this invention has been described in reference to a particular embodiment, it will be understood that this invention is also capable of further embodiments within the spirit and scope of the appended claims.

I claim:

1. A multiple site laser excited pollution monitoring system, comprising:
    a laser situated at one preselected location, said laser producing an output beam of electromagnetic radiation at a predetermined wavelength;
    a beam deflector optically aligned with said laser beam for deflecting said laser beam in a predetermined timed sequence to a plurality of distinct different positions;
    means for receiving each of said deflected laser beams at each of said distinct different positions and for transmitting each of said deflected laser beams at said predetermined sequence of time to a plurality of other preselected locations remote from each other and from said one preselected location;
    a plurality of laser excited photoacoustic pollution detectors, each of said laser excited pollution detectors being located at a different one of said other preselected locations and each of said detectors receiving each of said deflected laser beams, respectively, at a different time in accordance with said predetermined timed sequence;
    each of said laser excited pollution detectors providing an electrical output signal representative of the presence of pollutants at said plurality of other locations, respectively;
    a separate electrical wire connected to each of said laser excited pollution detectors for transmitting each of said electrical output signals to said one preselected location; and
    means located at said one preselected location for connecting thereto each of said separate electrical wires and for receiving each of said electrical output signals from said pollution detectors, analyzing said signals, and providing an output indicating the presence and quantity of pollutants present at each of said plurality of other preselected locations.

2. A multiple site laser excited pollution monitoring system as defined in claim 1 wherein said receiving and transmitting means comprises a plurality of optical fibers.

3. A multiple site laser excited pollution monitoring system as defined in claim 1 wherein said signal receiving, analyzing and output providing means comprises a signal processor and display unit.

4. A multiple site laser excited pollution monitoring system as defined in claim 1 further comprising a plurality of lasers at said one location, each of said lasers producing an output beam of electromagnetic radiation having at least one predetermined wavelength and means optically interposed between said plurality of lasers and said directing means for transferring said laser output beams to said beam deflector.

5. A multiple site laser excited pollution monitoring system as defined in claim 4 wherein said means for transferring said laser output beams comprises a plurality of beam splitters.

6. A multiple site laser excited pollution monitoring system as defined in claim 5 wherein said receiving and transmitting means comprises a plurality of optical fibers.

* * * * *